United States Patent [19]

Stickl

[11] 4,057,627

[45] Nov. 8, 1977

[54] ACNE PREPARATION FOR ORAL ADMINISTRATION

[75] Inventors: Helmut Anton Stickl, Strarenweg 6, 8033 Krilling, near Munich, Germany

[21] Appl. No.: 587,988

[22] Filed: June 18, 1975

Related U.S. Application Data

[63] Continuation of Ser. No. 343,096, March 20, 1973, abandoned.

[30] Foreign Application Priority Data

Mar. 21, 1972 Germany .............................. 2213677
Feb. 8, 1973 Germany .............................. 2306223

[51] Int. Cl.$^2$ ............................................. A61K 39/02
[52] U.S. Cl. ........................................ 424/92; 195/96
[58] Field of Search ........................................... 424/92

[56] References Cited

U.S. PATENT DOCUMENTS 3,651,214  3/1972  Raettig .................................. 424/92

OTHER PUBLICATIONS

Engman, J. Amer. Med. Ass., vol. 76, pp. 176–177 (1921).

*Primary Examiner*—Dolph H. Torrence
*Attorney, Agent, or Firm*—Gordon W. Hueschen

[57] ABSTRACT

An acne preparation for oral administration and a method of preparing the same in which a nutrient medium, such as, meat-peptone broth is inoculated with *Corynebacterium acnes*, such as, Beck, Gerrath and Vogel strains and combinations thereof, fermentation is carried out, the *Corynebacterium acnes* are inactivated, preferably by treatment with ultrasonics, and freeze-dried, to form an immunizing constituent. This immunizing constituent is preferably mixed with metabolic products of *Corynebacterium acnes* as a desensitizing constituent, preferably antigens contained in the nutrient medium in which *Corynebacterium acnes* are cultivated. The composition may be made in the form of tablets, capsules or liquids, such as, emulsions or syrups, and may contain conventional adjuvants, carriers and/or auxiliary agents.

26 Claims, No Drawings

ACNE PREPARATION FOR ORAL ADMINISTRATION

This is a continuation of application Ser. No. 343,096, filed Mar. 20, 1973, now abandoned.

The present invention relates to an orally administered preparation for treating acne vulgaris.

Acne vulgaris is a disease of the sebaceous gland-sebaceous follicle apparatus. It manifests itself as a cornification disturbance which begins at the opening of the sebaceous gland excretory ducts in the hair follicle canal and extends from there to the epidermis surface. The disease occurs in puberty and becomes apparent in the form of inflamed sebaceous glands, which are also designated as pimples, papules or pustules, on the face, on the chest, and on the back.

The inflamed efflorescences generally heal with the drainage of a fatty-sebaceous mass, the so-called blackheads, which are often mixed with pus and which, after healing, leave disfiguring scars.

In the classical treatment of acne vulgaris, local therapeutics were prescribed which contained sulfur, ichthyol, resorcin, and salicylic acid. SCHNEIDER (W. Schneider, "Experiences with a New Acne Therapy", German Medical Weekly, V. 91, [1966], p. 2017), and TRONNIER (H. Tronnier, "Akne vulgaris", Folia Ichthyolica No. 15) have proposed an acne therapy which is based on the principle of applying to the acne skin an emulsion containing an excess of an emulgifying agent, consisting of alkylated esters of phosphoric acids. Treatment of the skin surface lipids by means of a systematic long-term therapy with tetracyclines has been proposed in the past. However, despite many and greatly varying therapeutic proposals, no sufficiently effective, satisfactory treatment, that would assure rapid healing of the disease, has been known to date.

Significant for an immunogetic treatment is the realization that, particularly in the inflamed form of the disease with the formation of small blisters and reactive scars of the skin tissue, Corynebacteria acnes (hereinafter referred to as C. acnes) always participate in the disease of the skin, which is an ubiquitous, widely spread eruption of the healthy skin and, respectively, of the sebaceous glands, and whose causal importance in the occurrence of acne vulgaris has been considered uncertain for a long time (F. A. LENTZE, Abl. Bakt. Hyg. Orig. 155 [1950]pages 290–294; A. WISKEMANN, Padiat. Prax. 10 [1971] pages 579–584). Today it is a known fact that the sebaceous gland excretory ducts in the follicle openings of acne sufferers are colonized with C. acnes having particularly active, lipolytic ferments. C. acnes free more fatty acids from the sebum of acne sufferers than in the case of people who are not affected by acne, and more than can be done by other bacteria. Fatty acids favor, on the one hand, the growth of the acne bacteria in the hair follicles and thereupon lead to the direct irritation of the tissues immediately adjacent the efflorescence. On the other hand, the acne bacteria and their metabolic products themselves lead, in the course of time, to allergic reactions of the retarded type which may become apparent in the proliferation of reticular cell elements and, in the second stage of the acne, in the formation of small blisters.

An immunization treatment with a vaccine should, therefore, act best in the second stage which is characterized by tissue-allergic phenomena, and in which the local therapeutics employed heretofore fail. As early as 60 years ago a vaccine was therefore developed from C. acnes and used experimentally (Alexander FLEMING in "Lancet" 1909, pages 1035–1038). While some authors have confirmed successful treatments between 1910 and 1921, others could not do likewise, and no further reports concerning such treatments can be found after about 1921. The treatment of acne vulgaris with vaccines was heretofore based on vaccine injection in which the quantity of the injected destroyed C. acnes could not be measured reliably. The reason for this must be considered to reside in the fact that C. acnes multiply in firmly cohesive cellular units of hundreds to several thousand bacteria.

A further disadvantage of the treatment by vaccine injection is that the injection of inactivated strains of C. acnes leads to an additional allergenicity. After the injection, there occurs regularly an outbreak of the acne efflorescence frequently having a considerable extent. Moreover, these bacteria antigens are not well tolerated in case of injection. The cause thereof is the formation of precipitating antibodies which, during the reaction with the antigen in the tissue, lead to an Arthus phenomenon like reaction and, also increase the Arthus phenomenon characterizing the inflammation reaction of the acne efflorescence. The dosage of the injections must therefore be increased slowly in 6 to 8 small individual injections and must not exceed a maximum of $10^4$ germs per strain and per injection. At that time, there will be produced, initially, an allergenicity and, accordingly, during the cautious treatment of man, the outbreak of the focal acne points in the face; the partial melting-down thereof and, in unfavorable cases, an immunogenic polyneurities. When the dosage of the injection is lowered, however, the success becomes uncertain.

It has previously been attempted (vaccine of the MERIEUX Company Institut Merieux, 17 Rue Bourgelot, 69 Lyon, France) to add to a low acne bacterium dose other antigens which originate with the usual saprophytic accompanying germs (for example, skin streptococci, among others). This was to have the effect of controlling the ubiquitous germs secondarily involved in the melting-down processes of the foci in the florid acne. The successes of these attempts remain unsatisfactory.

Further disadvantages of the injection method are that the Beck and Gerrath strains, which are nearly identical, can be combined well, but the addition of the Vogel strain causes difficulties with regard to tolerance, and urea is not usable as an adjuvant.

The uncertain efficacy, the varying success of the treatment or healing, an often temporary increase of acne vulgaris with acute inflammatory phenomena and undesirable complications would therefore seem to indicate that the treatment of acne vulgaris with an injected vaccine is not a satisfactory therapy.

It has now been found that it is possible to eliminate the disadvantages and drawbacks described above relative to the injected vaccines, by means of a composition which is characterized by the fact that it can be administered orally, and that it contains an immunizing constituent, preferably together with a desensitizing constituent. Contained therein as the immunizing constituent is inactivated C. acnes, and as the desensitizing constituent metabolic products of bacterium acnes. The customary adjuvants, carriers and/or auxiliary agents may also be provided, if such is desired.

Preferred as the principle immunizing constituent are the Beck, Gerrath, and Vogel strains, since they are not very toxic, hardly allergetic, and immunize well. These strains are deposited at the Bavarian State Inoculation Institute, Munich, the Hygiene Institute of the University of Cologne; Erlangen (Beck GA 1/69 [Nr. 17]; Gerrath CA 11/69 [Nr. 13]; Vogel CA 111/69 [Nr. 19]); the International Center for Information on a Distribution of Type Cultures, Lausanne, 19 Ave. Cesar Roux (Beck La 1159; Gerrath La 1162; Vogel La 1166), the American Type Culture Collection, 12301 Parklawn Drive, Rockville, Maryland 20852 (Beck 21911; Gerrath 21912; Vogel 21913) and the Fermantation Research Institute, Agency of Industrial Science & Technology, No. 8-1 Inage, Higashi-5-chome Ciba-shi, Chiba-ken, Japan.

The numerical ratio of the strains contained in the composition according to the present invention may vary within wide limits. The bacteria strains of Beck, Gerrath and Vogel are preferably employed in a ratio of 1-3:1-3:0.5-1.5, particularly about 2:2:1, and at a dosage of $5 \times 10^9$ germs per treatment. Very good results have been obtained with the administration of approximately 10-20, preferably about 15 billion germs.

The following is a morphologic and taxonomic classification of the C. acnes.

The description of the C. acnes with regard to Morphology and the system is thoroughly described in Bergey's Manual of Determinitive Bacteriology, Baillere, Tindall and Cox Ltd., VII. Ed., 1957, pages 595, No. 29.

C. acnes are gram positive unmoveable rods, which are not acid resistant and sometimes grow with single or double sided column-formed swelling, often possessing the appearance of granulation. The C. acnes typically can be dyed according to Neisser with a Blue-Violet solution (Methyl blue-crystal violet). The Polar bodies herewith take on a dark appearance. It is typical for the C. acnes to become conglutinated into groups whereby the individual rods which are 5 to 7 times longer than wide, often lie next to each other at V-formed angles. This tendency to conglutination makes counting of the C. acnes very difficult (Ultrasonic treatment for counting).

All 3 strains of the C. acnes vary significantly in their morphology. In pure cultures, coccus-like elements are mixed together with rod-like and pole-shaped bodies. In older cultures, grains, i.e. coccus-like bacteria, appear more frequently than rod-shaped bacteria.

TAXONOMY

The culture classification of the C. acnes, identifies itself by having typical growth characteristics and by specific conglutination by antiserum. In contrast to the Corynebacterium diphteria which is the main representative of the Coryne group, the acne bacteria identify themselves by growing in acidic serum Agar or by growing in glycerin containing bouillon, with a pH of 6.8. Acne bacteria dissolve gelatin. Diphteria bacteria do not. In addition, acne bacteria develop catalases.

Limited growth takes place under aerobic conditions, whereas optimal growth takes place under anaerobic culture conditions.

While the Vogel strain slowly multiplies under strict anaerobic growth conditions, the Beck strain shows a fast multiplication, which also occurs under less stringent anaerobic conditions. The growth is very apparent in acidic mediums and with the addition of 2% glycerin.

The Gerrath and Vogel strains, with a specific antiserum of the Beck strain, will likewise conglutinate but to a lesser degree. We have found here, that the antigenetic relationship between the Beck and Gerrath strains is very high, while in contrast to the Vogel strain, the antigenetic relationship (common partial antigen) is clearly lower.

Serum conglutination occurs with specific antiserum against the C. acnes Beck strain of 1:256, as against the Gerrath strain of 1:128 to 1:256 ±, or as against the Vogel strain of 1:68.

Generally it can be said that all freshly isolated strains of acne patients may also be used, provided they do not have any toxic or too strongly allergenic properties. Attenuated strains of C. acnes therefore are preferred, in particular in inactivated form.

The preparation of the strains of C. acnes may be accomplished in a manner known per se. Preferably it is accomplished by cultivating C. acnes on a suitable nutrient medium, such as a liquid meat - peptone nutrient medium at practically neutral conditions (pH 7 ± 0.1), with the exclusion of air, and inactivating the same, for example by heating, mixing with phenol (about 0.2%) or formalin (about 0.2-0.4%), mixing with acetone in the cold and precipitating and/or by treating with ultrasonics.

The treatment, by means of ultrasonics, of the bacteria which are being inactivated is the preferred form in order to release them from the very firm cellular units formed during the propagation thereof. After centrifuging, the inactivated bacteria obtained are freeze-dried in a known manner and preferably provided with a hydrophilic additive which enhances the persorption by the stomach and intestinal walls, such as, particularly urea, for solid preparations, or sugar and mucins for liquid preparations (emulsions or syrups).

According to a preferred embodiment, the inventive preparations contain inactivated strains of C. acnes in freeze-dried form. This embodiment affords the additional advantage that peptone may be employed as auxiliary agent for the freeze-drying operation, which, differing from customary processes, was previously needed as nutrient medium of C. acnes Gerrath, and thus contains metabolic products of C. acnes. This pretreated peptone contains surface-active amines, as well as the afore-mentioned desensitizing constituent. By virtue of the surface-active amines, a good distribution of the antigen in the lymphatic organs of the intestines is effectively achieved. In contrast thereto, the use of biogenic amines in injected vaccines is not suggested because of their toxic circulatory effect.

However, they are not toxic, on the other hand, when taken orally.

The heretofore practiced use of inactivated strains of C. acnes in the form of injected vaccines led, as has been set forth hereinabove, to an additional allergenicity and formation of precipitins as antibodies, and therewith to an increase of the Arthus phenomenon. This form of allergy disturbs the therapy. It has now been surprisingly found that not only can additional allergenicity be prevented when the antigen component is administered orally, but that even an existing allergy against C. acnes, in the sense of a desensitization, can be eliminated.

Used as desensitizing component are metabolic products of C. acnes which act in a desensitizing manner without disturbing the immunizing antigenic effect. This component may be yielded particularly from the medium of acne cultures. The fraction of the C. acnes nutrient medium containing the antigens may be advantageously employed. What is involved are essentially lipopolysaccharides. The elimination of the undesirable allergy form takes place within a very short period of time in the case of oral intake.

The supply, or administration, of the corpuscular antigen, i.e. of the bacteria themselves, leads accordingly to tissue immunity and not to an allergy with the oral application. The specific acquired protective reaction of cells and tissues prevents an unrestrained spreading and increase of germs. The germs disappear from the skin, and a healing effect will be produced without supperation, such as, for example, in the case of the injection treatment, within 21 days. Thus, in the present invention, with the oral administration, there exists a different immuno-physiology which could not be expected.

The possibility of immunizing orally and of simultaneously desensitizing represents an unexpected result.

As an immuno-adjuvant, the present vaccine preferably contains urea as well as surface-active biogenic amines of the peptone serving as nutrient medium. The latter may simultaneously serve as auxiliary agent for the freeze-drying operation, as has been set forth hereinabove. If *C. acnes* Gerrath is used for the preliminary treatment of the peptone, no toxic secondary products will be formed. The fact that urea acts as an immuno-adjuvant in the oral application of acne antigen was not known heretofore.

The manufacture and administration of the inventive acne preparation will now be described in further detail hereinafter on the basis of several examples.

EXAMPLE 1 a. Medium

A nutrient solution, consisting of 2300 ml meat-peptone broth (pH 7 ± 0.1) and 600 ml Sörensen's buffer (pH 7.1) is sterilized for 1 hour in the autoclave at about 120° C. 60 ml of pure glycerin were added and the nutrient medium was transferred to 300 ml Erlenmeyer flasks in a volume of 300 ml/flask, so that the flasks are filled to the beginning of their narrow necks. A layer of pure liquid paraffin (Nujol), was placed on the surface of the nutrient medium, and the flasks were maintained for 60 minutes in a steam bath at 100° C. Before the nutrient medium had cooled, the flasks were closed with gauze stoppers saturated with a mixture of hot beeswax and hard paraffin to exclude atmospheric air. After cooling to 35° C. the medium contains practically no adsorbed oxygen. Inoculation is effected with *C. acnes* through the layer of liquid paraffin with Pasteur pipettes.

b. Inoculation with *C. acnes*

Inoculum was obtained from storage (standard) cultures (nutrient agar in shallow Fortner-dishes, rim 10 mm high, with additive of 2% glycerin, incubated anaerobically according to Fortner), and suspended in meat-peptone broth. Massive inoculation of the flasks was carried out.

c. Culture and Harvest of the Organisms

Incubation: 10 days at a temperature of about 30-32 C°. Samples were obtained from the culture flasks for purity assurance. A 5% phenol solution 1:10 (= 0.5% phenol concentration in the culture medium) was added. After a reaction time of 24 hours the flasks were heated for 2 hours at 60° C., and then allowed to cool.

For the purpose of desegregation of the bacteria, ultrasonic treatment was carried out for 30 seconds with a 500 W initial output. For subsequent adjustment of the tablets, counting of the bacteria in a counting chamber was carried out. Control cultures were prepared to assure that all organisms are killed. When the control cultures remain sterile for a 10-day period, the bacteria were harvested by centrifugation (20 minutes at 3500 r.p.m. = about 8000 X g). The sediment consisting of *C. acnes* was mixed, depending on the number of organisms, with 1/20 or 1/10 of supernatant culture medium. The culture medium and the residues of peptone serve as a coadjuvant excipient for lyophylization and contains, in addition to minimal residues of glycerin (not considered a contaminant), surface active, low-molecular, dialysable amines. This procedure was followed by freeze-drying. The supernatant medium from each culture flask, in a volume of at least 30 ml from each flask (1/10 of the initial volume), was administered by intraperitoneal injection to groups of guinea pigs (free of potential contamination by Botulinus bacteria and Botulinus toxins). The guinea pigs received the same volumes by intragastric administration via a stomach tube. Observation period: 14 days.

d. Desensitizing Fraction

The supernatant culture media of *C. acnes* Gerrath or Beck were transferred to sterile dialysis membranes which are suspended in a recently defrosted refrigerator. Cold-induced pervaporation via the membrane reduced the medium within 1 week to ¼ of the initial volume. The residual material was lyophilized. A whitish, freeflowing hygroscopic powder was obtained which was added to lyophylized *C. acnes*, strains Beck, Gerrath, and Vogel. Urea was added in equal parts by weight. The tablets were adjusted to a bacteria concentration assuring that each tablet contained a minimum of 1 billion organisms. The bacterial strains Beck, Gerrath, and Vogel were combined at a ratio such that the strains Beck and Gerrath, calculated as dry weight, are present in at least double the concentration of strain Vogel, e.g. 1 Beck : 1 Gerrath : 1 Vogel, normally 2 Beck : 2 Gerrath : 1 Vogel.

The dry mass of the tablets contained the *C. acnes*, culture medium of all three strains and dialyzed culture medium of the Gerrath strain, in amounts between about 8 and 20 mg, and urea, in an amount of at least about 30% by volume as an immuno-adjuvant. After compression, 25 tablets each were placed in bottles and maintained in an inert atmosphere. This improves the preservation of the preparation.

EXAMPLE 2

Administration of the Acne Preparation a. 5 Tablets each on 5 successive days were administered to a 27-year old secretary affected with acne of the face (stage 11), who had been treated without success for 9 years with solutions, ointments, ovulation inhibitors (hormones), and antibiotics. The dispensation was made in the morning, in each case 30 minutes before the meal (1 series). The tablets were taken without complaint and no general symptoms of any kind occurred. On the fifth day of taking medication, as well as during subsequent controls (see below), examination of the transaminases (SGOT, SGPT) and of the urine were made. On the eighth day, and still more clearly on the 10th day, after first taking the tablets, diminishing of redness and infiltration around the acne efflorescences occurred. On the 21st day, distinct improvement, with general retrogression and resorption of the efflorescences, took place. Control after four and after fifteen months showed healing of the acne (residual scars).

b. The administration was made to a 22-year old man, with acne conglobate (stages 11–111) of the face with numerous scars and who had been treated without success for 6 years with different remedies. He was given five tablets each day for 5 days, in the morning and on an empty stomach. After temporary recession of the redness and itching sensation of a large efflorescence at the right zygomatic arch, renewed inflammatory reddening occurred. Therefore, on the 28th day after beginning the treatment, a second series of five tablets each day for 5 days were given 2 weeks later (43rd day after beginning of the treatment) by a further similar series. 4 To 5 days after beginning of the second series distinct improvement occurred. 2 Weeks after the third series, no more inflammatory redness was present and efflorescences were resorbed, except for minimal residues. Control after 10 months showed healing of the acne. On the fifth day after the beginning of the treatment as well as on the occasion of subsequent treating series and visits, examination of the transaminases (SGOT and SGPT) and of the urine were conducted with no special findings.

EXAMPLE 3

Acne syrup—An acne syrup was prepared containing 1-billion acne bacteria per cc of syrup. The syrup contained only the Beck and Gerrath strains of *C. acnes* (freshly isolated with low pathogenicity in the animals).

Twelve cases of severe acne, including nine patients with acne conglubata were treated. The treatment consisted of the administration of a total dose of 20-billion bacteria in a first cycle and 40-billion bacteria in a second cycle (beginning on the 20th day after the beginning of the treatment).

On the 10th day the patients showed little or no improvement.

On the 20th day following the beginning of the treatment, obvious improvements were observed in 10 of the 12 patients.

A control group of six patients was initially treated with placebo (solvent without acne bateria). This treatment resulted in no improvement of the patients. Thereafter, the control group was administered acne syrup at a total dosage of 20-billion bacteria over a period of ten days. From the 11th to the 15th day after initiation of the treatment a total dosage of 40-billion bacteria was given. Improvement was thereafter noted by the regression of postules, nodules, and abesses.

EXAMPLE 4

Acne tablets, of essentially the same composition of those of Example 1 and containing the Beck and Gerrath strains were administered to 23 patients having mild to moderate acne (also patients with stage 1 acne). After administration of 20-billion bacteria, over a 10 day period, no visible effect was observed in four cases, a moderate effect was found in eight cases, satisfactory results were obtained in the latter eight cases after a second cycle of treatment at a total dosage of 20 tablets on the 20th through 25th days after initiation of the treatment, and good results were obtained in 11 of the 23 patients after a single cycle of treatment.

EXAMPLE 5

Twenty-six patients, with cases of acne vulgaris, several cases of severe acne aggregata, and one case of acne conglobata, were treated, pathological cutaneous manifestations of variable intensity and extent having existed for an average of up to 4½ years. Conventional polypragmatic treatment failed to produce results.

The treatment consisted of the administration of tablets, of essentially the same composition as those utilized in Example 4, with urea as an immuno-adjuvant but without a desensitizing constituent and using the same cycle of treatment as utilized in Example 4. No results were obtained in four cases, unsatisfactory results were obtained in four cases due to rapid relapse, satisfactory results were obtained in nine cases (requiring a second cycle of treatment) and very good results were obtained in nine cases, in which a second cycle was not required. The latter group of nine patients did not develop any manifestations after an observation period of several months.

No good or successful results were noted in a control group of 10 patients treated with conventional therapy (Icthyol ointment, Vitamin A, acid solutions and creams and antimicrobial therapy). Obvious improvement was achieved in five cases, while the results were inadequate in the other five cases, all patients had been hospitalized. The control group was then changed over to treatment with acne tablets.

There were no indications of intolerance involving skin, the gastrointestinal tract, or general disposition of patients treated with acne tablets.

EXAMPLE 6

A group of 19 patients were given acne syrup with 1-billion bacteria per ml. of syrup and containing no immuno-adjuvant or desensitizing constituent. All patients suffered from severe acne with acne conglobata in 11 cases. The patients were given 5 ml. of acne syrup on each of 5 consecutive days. Eight other patients with acne received acne tablets, with the same dosage of 1-billion bacteria per tablet, at a rate of five tablets per day for 5 days.

In 14 patients, obvious improvement was observed 10 days after the treatment with satisfactory improvement of cutaneous manifestation observed on the 20th day in most patients. A complete cure of eruptions with absorption of papulous-pustular was achieved in one patient within 20 days after initiation of the treatment. Thus, results were obtained in 15 of 19 patients. One patient with "oily acne" was included in the group but did respond to the treatment. In this case it was not expected that results would be obtained with acne syrup.

Eight patients were treated by standard acne therapy at the beginning of the trial (mainly topical, Vitamin A-acid, antibiotics) to serve as controls. In only three cases were satisfactory improvements seen within the observation period of 29 days. Results of treatment were moderate to unsatisfactory in five patients. All eight patients were treated subsequently with acne tablets with good results in six of eight cases. In contrast to the procedure followed with the previously mentioned 19 patients, findings were not monitored each day, i.e., the patients reported only once per week to the outpatient clinic. Signs of intolerance were not observed after either the use of the acne syrup or the acne tablets. Changes in blood values (transaminases, urea-N, differential blood picture, leucocyte count, coler index, immunoelectrophoresis) were not observed. All patients were examined thoroughly when treatment was initiated and at the end of treatment (21-28 days after the initial injestion of the test drug).

In contrast to the vaccine designed for injection, the use of the present inventive preparation further renders possible the utilization of different *C. acnes* strains at a large dosage and with good tolerance. There arises no harmful allergenicity impairing the applicability of the vaccine; for example, no increase outbreak of the acne foci, no suppuration, and no general symptoms such as fever and swelling of the lymph nodes will occur. Since the inventive preparation is tolerated without reaction, an upper dosage limit cannot be given. For example, daily administration of 20 billion bacteria in a period of 4 days and 24 billion bacteria in a 5 day period, has resulted in no adverse effects. On the other hand, it has also been found that, in rare cases, dosages as small as 2.5 billion bacteria per day may have a good effect. As a result of considerable experimentation, it has been determined that it is preferable to administer 5 billion bacteria per day during a 4 day period by way of capsules, each containing 2.5 billion bacteria.

While the strains Beck, Gerrath and Vogel are preferred, other strains of *C. acnes* can be utilized in accordance with the present invention. As previously pointed out, it is advantageous to utilize the strains Beck, Gerrath and Vogel because of their non-allergenic and non-toxic properties.

Where less than all three of the strains Beck, Gerrath and Vogel are utilized, it is also preferable to utilize a combination of two as opposed to a single strain. Examples of such combinations are, of course, Beck and Vogel, Gerrath and Vogel, and Beck and Gerrath.

As previously pointed out, the *C. acnes* can be administered in the form of solids or liquids. Any of the well-known oral pharmaceutical forms may be used, such as dragées, tablets, pills, lozenges, syrups or capsules. Dragées, tablets and pills may also be characterized by talc and/or carbohydrate carrier or builder or the like being preferably lactose, and/or corn starch and/or potatoe starch. With syrups and lozenges, a sweetened vehicle is generally employed. Capsules may be in the commonly used hard or soft forms. For example, the hard capsules are generally utilized with a powdered form of the medicament and are made of a water-soluble plastic material, e.g., gelatin or methyl cellulose. The soft capsules are normally made of a water-soluble plastic material, e.g., gelatin, plasticized with, for example, glycerin (i.e., glyco-gelatin). Specifically, a liquid preparation has been obtained containing the *C. acnes* and cane sugar syrup in a vegetable mucous material. Tablets have also been prepared using milk sugar.

While meat-peptone broth has been utilized as the nutrient solution in most instances, any other nutrient media having a pH between about 6 and 7 and a high content of carbohydrates and/or glycerin together with ingredients promoting anaerobic growth of *C. acnes* can also be used. Suitable growth media include thioglycolate-bouillon; thioglycolate-glucose-bouillon; glycerin (2%)-glucose-bouillon; glucose (2-4%) bouillon, etc.

In general, as has been previously indicated, anaerobic conditions are preferably maintained. It has been found that the growing conditions of the strain Beck are less restricted than for the other strains. In fact, the strain Beck can be grown under aerobic conditions.

With the aid of the preparation, it is possible to successfully obviate all the disadvantages of the injection treatment while nevertheless increasing the useful effect. The inclusion in the vaccine of secondary infectious germs, which is really nothing but a dilemmatic solution that is not without risks, is not necessary in the case of the present inventive preparation.

It will be obvious to those skilled in the art that many modifications may be made within the scope of the present invention without departing from the spirit thereof, and the invention includes all such modifications.

What is claimed is:

1. An acne composition for oral administration, comprising inactivated *Corynebacterium acnes* as an immunizing constituent and a pharmaceutically-acceptable carrier therefor.

2. The acne composition of claim 1, comprising metabolic products of *Corynebacterium acnes*, contained in the nutrient medium in which said *Corynebacterium acnes* are cultivated, as a desensitizing constituent.

3. A composition in accordance with claim 1 wherein the inactivated *Corynebacterium acnes* are selected from the group consisting of Gerrath, Beck and Vogel strains and combinations thereof.

4. The composition of claim 1 which additionally contains urea as an immuno-adjuvant.

5. The composition of claim 1, wherein the *Corynebacterium acnes* are in freeze-dried form.

6. The composition of claim 1 wherein the composition is in the form of a tablet, capsule, or liquid.

7. The theraputic composition of claim 1 in unit dosage form comprising at least 1 billion of *Corynebacterium acnes*.

8. A composition as defined in claim 7 in which the *Corynebacterium acnes* strain is Gerrath.

9. A composition as defined in claim 7 in which the *Corynebacterium acnes* strain is Vogel.

10. A composition as defined in claim 7 in which the *Corynebacterium acnes* strain is Beck.

11. The composition of claim 11, in which said *Corynebacterium acnes* are a combination of at least two *Corynebacterium acnes* strains selected from the group consisting of Beck, Gerrath and Vogel.

12. The composition of claim 11 wherein the strains Beck, Gerrath and Vogel are present in the ratios of 1-3:1-3:0.5-1.5.

13. The composition of claim 11 wherein the strains Beck, Gerrath and Vogel are present in the ratio of 2:2:1.

14. The composition of claim 7 in the form of a tablet, capsule, or liquid.

15. The composition of claim 7 wherein at least one of the components is lyophilized.

16. The composition of claim 7, which additionally includes metabolic products of *Corynebacterium acnes* from the culture medium in which said *Corynebacterium acnes* are cultivated.

17. A composition as defined in claim 16, wherein the metabolic product is an antigen-containing fraction of the culture medium of *Corynebacterium acnes*.

18. The composition in accordance with claim 7 which contains a non-toxic adjuvant material.

19. The composition of claim 7 which additionally contains urea as an immuno-adjuvant.

20. A composition in accordance with claim 1 wherein the composition is in the form of a liquid.

21. A method of treating acne infection in man by oral administration of a composition according to claim 1.

22. The method of treating acne infection in man according to claim 21 wherein urea is employed as an immuno-adjuvant.

23. A method of treating acne infection in man by oral administration of a composition according to claim 2.

24. A process for producing an acne composition for oral administration, comprising cultivating *Corynebacterium acnes* in a nutrient medium under anaerobic conditions until substantial growth of said *Corynebacterium acnes* has occurred, recovering said *Corynebacterium acnes* from said nutrient medium and mixing at least a portion of the metabolic products of said *Corynebacterium acnes* contained in said nutrient medium with said *Corynebacterium acnes*.

25. A process in accordance with claim 24 wherein the metabolic products in *Corynebacterium acnes* are a mixture of said *Corynebacterium acnes* of the Gerrath, Beck and Vogel strains.

26. A process for producing an acne composition for oral administration, comprising cultivating *Corynebacterium acnes* in a nutrient medium under anaerobic conditions until substantial growth of said *Corynebacterium acnes* has occurred, recovering said *Corynebacterium acnes* from said nutrient medium and mixing urea with said *Corynebacterium acnes*.

* * * * *